United States Patent [19]

Desai

[11] Patent Number: 5,616,687
[45] Date of Patent: Apr. 1, 1997

[54] COUPLING REAGENT AND METHOD

[75] Inventor: Manoj C. Desai, Mystic, Conn.

[73] Assignee: Pfizer Inc., New York, N.Y.

[21] Appl. No.: 435,904

[22] Filed: May 5, 1995

Related U.S. Application Data

[62] Division of Ser. No. 56,261, Apr. 30, 1993, Pat. No. 5,416,193.

[51] Int. Cl.$^6$ .................................................. A61K 38/02
[52] U.S. Cl. ........................ 530/334; 530/333; 530/338; 530/339; 530/344
[58] Field of Search ................................... 530/333, 334, 530/338, 339, 344

[56] References Cited

U.S. PATENT DOCUMENTS 4,102,877  7/1978  Nutt .

OTHER PUBLICATIONS

Wolman et al., Chem. Commun., 629–630, (1967).
Weinshenker et al., Oganic Syntheses, Collective Vol. 6, pp. 951–954 (1990).
Weinshenker and Shen, Tetrahedron Letters No. 32, pp. 3281–3284, (1972).
Williams and Ibrahim, Chem. Rev. 81, pp. 589–636, (1981).
R.B. Merrifield, J. Am. Chem. Soc. 85, pp. 2149–2154, (1963).
Akelah and Sherrington, Chem. Rev. 81, pp. 557–587, (1981).
Sheehan et al., J. Org. Chem., 26, pp. 2525–2528, (1961).
Weinshenker et al., Organic Syntheses, Collective vol. 6, pp. 218–219.
R. B. Merrifield, Science, vol. 150, pp. 178–185, (1965).
Fridkin et al., J. Am. Chem. Soc., 88 (13), 3164–3165.
Angew. Chem. Internat. Edit., 5 (3), 310 (1966).
Angew. Chem. Internat. Edit., 27 (2), 207–225 (1988).

*Primary Examiner*—David Lukton
*Attorney, Agent, or Firm*—Peter C. Richardson; Gregg C. Benson; James T. Jones

[57] ABSTRACT

A solid phase coupling reagent for amide formation, comprising insoluble polymer bearing pendant side chains, said side chains each comprising a terminal portion having the formula

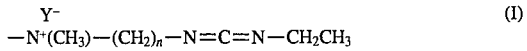

$$-N^+(CH_3)-(CH_2)_n-N=C=N-CH_2CH_3 \quad (I)$$

wherein $Y^-$ is a counteranion and n is independently an integer from 2 to 6; and a method of making amides employing the coupling reagent.

6 Claims, No Drawings

COUPLING REAGENT AND METHOD

This is a division, of application Ser. No. 08/056,261 filed on Apr. 30, 1993, now U.S. Pat. No. 5,416,193.

BACKGROUND OF THE INVENTION

This invention relates generally to a reagent and method for coupling amines with carboxylic adds to form amides.

Reacting an amine with a carboxylic acid to form a new species having an amide linkage is well known to the chemical arts. The reaction is generally implemented with a dehydrative coupling reagent.

Within the last thirty years solid phase synthetic procedures for coupling mines and carboxylic acids, for example to make peptides and polypeptides, have become well known in the chemical arts. The Merrifield solid phase synthesis, in both manual (JACS, 85, 2149, 1963) and automated (*Science*, 150, 178, 1965) forms is perhaps the oldest and best known method and functions by growing a polypeptide chain which is bound on an insoluble polymer. The chain is grown amino acid by amino add, with each new residue being added, in the presence of a coupling reagent, from a solution of the N-blocked acid. By attaching the growing peptide chain to an insoluble polymer, the Merrifield synthesis advantageously provides the peptide in a convenient form to be filtered and washed free of reagents and by-products.

In general, carbodiimides are known to be coupling reagents for the formation of amide linkages. In some instances a carbodiimide coupling reagent has been incorporated into a polymer, in what is in effect a variation on the Merrifield technique, to form a solid phase coupling reagent. For example, Wolman et. al., Chem. Commun., 629, (1967) report the use of an insoluble polycarbodiimide as a condensing agent in peptide synthesis, with best results reportedly obtained using polyhexamethylene-carbodiimide made by the catalytic decarboxylation of 1,6-diisocyanate hexane. This solid phase coupling reagent thus incorporates carbodiimide linkages as part of the polymer backbone.

Weinshenker et. al., *Tetrahadron Lett.*, 3281 (1972) and *Org. Synth.*, Coll. Vol. VII, 951, (1990) report synthesizing a polymeric carbodiimide by a detailed procedure involving (1) converting crosslinked chloromethylated polystyrene to polystyrene having pendant phthalimidomethyl groups; (2) converting the phthaiimidomethyl groups to aminomethyl groups; (3) treating the pendant aminomethyl groups with isopropylisocyanate to thereby make the corresponding isopropylureamethyl groups; and (4) dehydrating the urea moiety/to convert the pendant isopropylureamethyl groups to isopropyl carbodiimidomethyl groups. In contrast to Wolman et. al. as discussed above, the Weinshenker polymeric carbodiimide incorporates carbodiimide units as pendant groups rather than as part of the polymer backbone.

Nutt, U.S. Pat. No. 4,102,877 discloses using a Weinshenker-type of resin-bound carbodiimide in the cyclization of linear peptides.

SUMMARY OF THE INVENTION

This invention provides a dehydrative solid phase coupling reagent suitable for mediating the formation of amides comprising an insoluble polymer bearing pendant side chains, said side chains each comprising a terminal portion having the formula $$-N^+(CH_3)_2-(CH_2)_n-N=C=N-CH_2CH_3 \quad Y^- \qquad (I)$$

wherein $Y^-$ is a counteranion to the positively charged quarternary nitrogen and n is independently an integer from 2 to 6.

This invention further provides, in a broad aspect, a method of making an amide, comprising reacting an amine-functional reactant with a carboxylic acid-functional reactant, in the presence of an insoluble polymer beating pendant side chains, said side chains each comprising a terminal portion having the formula $$-N^+(CH_3)_2-(CH_2)_n-N=C=N-CH_2CH_3 \quad Y^- \qquad (I)$$

wherein $Y^-$ is a couteranion to the positively charged quaternary nitrogen and n is independently an integer from 2 to 6.

In a specific aspect, this invention further provides a method of synthesizing a peptide, comprising reacting a first reactant having the formula $$BG1-NH-R^1-COOH,$$

wherein BG1 is an amino blocking group and $R^1$ is the residue of an amino acid or of a peptide fragment, with a second reactant having the formula $$H_2N-R^2-COOBG2$$

wherein BG2 is a carboxylic acid blocking group and $R^2$ is the residue of an amino add or of a peptide fragment, in the presence of an insoluble polymer bearing pendant side chains, said side chains each comprising a terminal portion having the formula $$-N^+(CH_3)_2-(CH_2)_n-N=C=N-CH_2CH_3 \quad Y^- \qquad (I)$$

wherein $Y^-$ is a counteranion to the positively charged quaternary nitrogen and n is independently an integer from 2 to 6.

Thus a main aspect of this invention is the provision of a solid phase dehydrative coupling reagent comprising an insoluble polymer which can mediate the formation of amides. The polymer has pendant, carbodiimide-functional side chains, which terminate with groups having formula (I) containing a (positively charged) quaternary nitrogen. $Y^-$, the counteranion, will typically be chloride, although other anions such as bromide, iodide, mesylate, and trifluoroacetate are also suitable. As hereinafter further discussed and exemplified, this invention has wide applicability whenever a coupling reagent is required in an amide-forming reaction, such as for the formation of peptides and/or proteins. The coupling reagent can be used to make a plethora of known compounds including, but not limited to, the antihypertensives alfuzosin and captopril, the sweetener aspartame, the anxiolytic alpidem, and the antispasmodic clebopride. If the amide-forming reactants contain other groups which may be reactive under the reaction conditions employed, they can and should be protected, for example by conventional blocking groups of the type described, for example, in *Protective Groups in Organic Synthesis*, 2d Edition, T. W. Greene and P. G. M. Wuts, published by John Wiley and Sons, Inc. Generally the types of blocking groups employed for both amino and carboxyl groups are those which are well known and conventionally employed for the synthesis of peptides and exemplified below.

In the more specific application of peptide formation discussed above, the reactants which are useful are amino acids, particularly the commonly known α-amino acids, or peptide fragments containing two or more amino acid residues. The reactants, as noted, can be blocked to control which (amino or carboxyl) group reacts, as known in the art using conventional blocking groups. Conventional amino blocking groups include, for example, t-butoxycarbonyl (t-BOC), benzyloxycarbonyl (CBz), formyl, acetyl, trifluoroacetyl, toluenesulfonyl, and the like. Conventional carboxylic acid blocking groups include alkoxy groups resulting from conventional esterification with alcohols such as methanol, ethanol, propanol, t-butanol, and benzyl alcohol.

The term "residue" as it applies to an amino acid or peptide fragment means that portion of the acid or fragment exclusive of the amino and carboxylic acid functionalities.

The present invention takes advantage of a particular class of carbodiimides to provide a solid phase carbodiimide coupling reagent. The reagent can be easily synthesized by combining a commercially available or readily synthesizable carbodiimide with any of a number of polymers which are also commercially available. No lengthy or cumbersome synthetic methodology is required.

DETAILED DESCRIPTION

Carbodiimide-functional compounds useful for making the solid phase coupling reagent of this invention have formula Ia:

$$N(CH_3)_2-(CH_2)_n-N=C=N-CH_2CH_3 \qquad (Ia)$$

wherein n is 2–6. The particular compound wherein n is 3, 1-ethyl-3-(3-dimethylaminopropyl)carbodiimide (EDC), is preferred because it is commercially available, for example from Sigma Chemical Co. The remaining compounds wherein n is 2, 4, 5, or 6 can be made along the lines disclosed by Sheehan et. al., *J. Org. Chem.*, 26, 2525, 1961, herein incorporated by reference. The procedure involves dehydration of the corresponding urea with p-toluenesulfonyl chloride and triethylamine in methylene chloride solution.

The solid phase coupling reagent can be made using a single compound of formula Ia, or a mixture of compounds having formula Ia. The polymer used to make the solid phase coupling reagent may also contain other, different side chains so long as the additional side chains do not interfere with amide formation.

Polymers suitable for use in making a solid phase coupling reagent according to the invention are widely known in the polymer arts and can readily be obtained from commercial sources. In general, a suitable polymer will comprise an inert backbone which contains pendant side chains containing groups reactive with carbodiimide-functional compounds of formula Ia. Ideally, the reactive group on the pendant side chain is a chloromethyl group. Such (chloromethyl-functional) resins are available commercially, as discussed below Other resins are also available with groups which can be converted to chloromethyl groups such as "Pam" resins of the formula

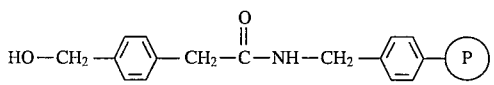

or "Wang" resins of the formula

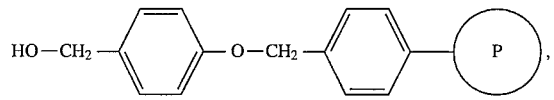

wherein Ⓟ represents the polymer backbone, both of which are available from Peptides International, Louisville, Ky. (see Peptides International Catalog, 1991–1992, pages 98–99). The terminal pendant hydroxymethyl groups on the above resins can be converted to chloromethyl groups by any of a variety of chemical methods known in the art. For example, the Pam or Wang resin can be reacted with an equivalent, or preferably an excess, amount of methane sulfonylchloride, in a suitable solvent such as chloroform and in the presence of a base such as a trialkylamine (e.g., triethylamine) to thereby form the corresponding mesylate. This reaction can be conducted by simply combining the resin, methanesulfonyl-chloride, and base in chloroform and stirring at room temperature for several hours, e. g. overnite. The mesylate can then be displaced by heating the mesylated resin with lithium chloride in dimethylformamide with stirring at 80°–140° C. The product resin is thus the same as shown above, with the terminal hydroxy groups replaced by chloro. This methodology is likewise applicable to any insoluble resin containing pendant side chains terminating with one or more hydroxymethyl groups.

Particularly preferred because of its ready commercial availability is chloromethylated polystyrene crosslinked by divinyl benzene. Polymers falling within this general class are available as beads in a large variety of mesh sizes and provide ready penetration of reagents even in the presence of swelling solvents. Examples of polymers suitable for use in making the solid phase coupling reagent disclosed herein include those having a size of 200–400 mesh, crosslinked with from 1–2% divinylbenzene, and having a level of chloromethylation of from about 0.3 to about 4.3 mmol Cl/g resin. These types of resins are available commercially, for example, from Peptides International, and from Fluka Chemie AG, Buchs, Switzerland under the designation Merrifield Polymer Fluka.

The solid phase coupling reagent of this invention can be synthesized by methods well known to the chemical arts. In the description which follows, chloromethylated styrene divinylbenzene is referred to for illustrative purposes only, end those skilled in the art will appreciate that any of the resins described above, or the like, can be employed. Typically the chloromethylated styrene divinylbenzene is combined with an mount of the desired carbodiimide functionalizing agent of formula Ia equivalent to the total amount of chloromethyl groups on the resin, or, preferably, with a slight excess thereof up to 50 mol % to enhance the rate of functionalization by the desired carbodiimide and to ensure that the reaction goes substantially to completion. Higher excesses of the carbodiimide functionalizing agent can be used but no significant advantage is believed to be provided thereby. The carbodiimide compound reacts with the chloromethyl groups on the polymer to functionalize the polymer in a manner which results in the formation of pendant quaternary carbodiimide side chains, as follows:

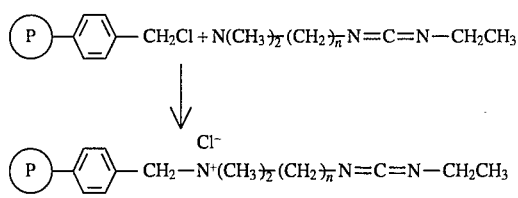

wherein Ⓟ represents the polymer backbone.

Once a pendant carbodiimide side chain has reacted to mediate the formation of an amide group, it forms a urea by-product, as follows:

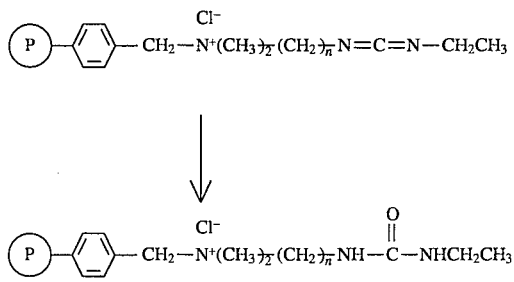

The resin can be regenerated, if desired, by dehydrating the pendant urea groups along the lines presented in Weinshenker et. al., supra. However, the resin is typically simply discarded.

The reaction to form the solid phase coupling reagent can be conducted in a suitable reaction vessel and a suitable solvent such as dimethylformamide (DMF), acetonitrile, tetrahydrofuran (THF), chloroform, or dioxane, with DMF and acetonitrile being preferred. A particular mode of implementing the reaction is simply to combine the chloromethylated resin with the carbodiimide functionalizing agent of formula Ia in an appropriate solvent and reflux the mixture for a period of time generally varying from a few (e.g. 2 hr) to 48 hr, with overnight reflux periods generally being sufficient to ensure substantial completeness of reaction. The reaction of chloromethyl groups on the polymer with added functionalizing agent of formula Ia is believed to proceed essentially to completion, thus yielding a polymer bearing carbodiimide-functional groups to about the same loading (mmol/g of polymer) as the loading of chloromethyl groups (or other reactive groups on the original polymer which will react with a compound of formula Ia and which will provide a suitable counteranion to form a pendant side chain comprising a terminal portion having formula (I)). The functionalized polymer can now be washed in succession with THF followed by diethyl ether, or with ether alone, and the product (i.e. the solid phase coupling reagent) isolated.

In an optimized procedure for making a solid phase coupling reagent, and as further exemplified in Example 1, EDC (or other compound of formula Ia) can be dissolved in a solvent such as DMF and combined with an insoluble polymer bearing dissolved in a solvent such as DMF and combined with an insoluble polymer bearing groups (such as the chloromethyl groups on the polymers previously mentioned) reactive toward EDC. The mole ratio of EDC to reactive groups is preferably about 1.2:1. Sufficient solvent (e.g. DMF) is added so that the molarity of EDC is about 1.1–1.5. The mixture is then heated to about 100° C. with stirring for several hours (e.g. overnite) to allow the EDC to react with the polymer. The mixture can then be filtered, washed, dried, and stored until needed to mediate an amide formation.

In a typical reaction in which a carbodiimide-functional coupling reagent, prepared as described above, is employed in an amide-forming reaction, an mount of solid phase coupling reagent bearing a total molar amount of carbodiimide groups at least equal to the moles of amide desired to be formed, is added together with equivalent amounts of carboxylic acid and amine, blocked as appropriate, to a suitable reaction vessel containing a suitable solvent such as chloroform, methylene chloride, dimethylformamide (DMF), or acetonitrile. In the event of solubility limitations of either the amine or carboxylic acid, t-butunol can be employed as a co-solvent, in an mount sufficient to effect dissolution. It is preferred to conduct the reaction with a slight molar excess of carboxylic acid-functional reactant relative to amine-functional reaction, say a molar ratio of carboxylic acid/amine of about 1.2 to 1. In general, no special precautions as to the dryness of the solvent need be taken. The reaction can be implemented with stirring, shaking, or other means of agitation. The coupling reaction will usually be allowed to proceed at a temperature of from about 15 to about 40° C., most often at about room temperature, for a period of from about 0.5 to about 48 hours. The supernatant containing a soluble product amide can then be separated from the resin by filtering, the resin can be washed with additional reaction solvent and the washings added to the supernatant, and essentially pure product recovered following solvent evaporation.

An alternative method which is preferred because it lends itself well to automation is to combine amino-functional reactant, an equivalent amount of carboxylic acid-functional reactant, and an amount of polymer bearing at least an equimolar amount of carbodiimide-functional groups in, as the reaction vessel, a vial fitted with an inert (e.g. silicone) septum. The vial plus reaction mixture can be mounted on a shaker, shaken for a pre-determined period of time, and the liquid containing the amide product sampled automatically by means of an automated syringe withdrawing the liquid through the septum.

Alternatively, the vial (or other reaction vessel) can be implemented at its bottom with a glass frit and pressure activated check valve. The vessel can then be shaken for a predetermined period and pressurized to force the liquid containing the desired amide product past the frit while retaining the solid phase coupling reagent behind in the reaction vessel. Advantageously, urea by-product remains attached to the solid polymer, thus separated from the final product.

The process of making an amide provided by this invention is not limited by or to any particular carboxylic acid or amine, and will function in mediating the formation of substantially any amide that will form in the presence of a non-solid phase (i.e., dissolved or solvated) carbodiimide. In particular, the amine nitrogen can be primary, or it can be secondary as, for example, by being contained within a ring or substituted by two separate groups, so long as at least one amine hydrogen which is sufficiently reactive, under the reaction conditions employed, is present to undergo amide formation. Classes of amines and exemplary members thereof include any amino-functional compound having an amine hydrogen capable of entering into an amide-forming reaction, including the following:

1. aralkyl amines such as benzylamine, 2-phenylethylamine, and 3-phenylpropylamine; The aromatic groups can be substituted by one or more substituents selected from, for example, alkyl, alkoxy, halo (e.g., fluoro, chloro, bromo, iodo), nitro, cyano, trifluoromethyl, and alkanoyl. The substituents just listed are listed to provide examples of the variety possible. The alkyl portion may likewise be substituted by one or more of said substituents, or the like. The particular substituent(s) are not believed to be critical unless, for example, their presence would lead to the formation of an unstable amide product.

2. aliphatic (acyclic) amines in general, the aliphatic portions of which can be branched or unbranched such as methylamine, ethylamine, n-propylamine, n-butylamine, n-pentylamine, n-octylamine, decylamine, any of which can be substituted by substituents of the type listed in (1). Disubstituted aliphatic amines are also feasible.

3. alicyclic amines such as cyclohexylamine, cyclopentylamine, cyclobutylamine, cyclopropylamine, any of which can be substituted by one or more substituents of the type listed in (1).

4. heterocyclic amines in which the amino nitrogen is a saturated ring atom—e.g., pyrrolidine, piperidine, morpholine, and piperazine.

It will be appreciated by those skilled in the art that the above examples are intended to be exemplary, not limiting, and that, as noted, virtually any amine having an amino hydrogen sufficiently reactive to participate in an amide-forming reaction will work as a reactant in the process of this invention.

The classes of carboxylic acids which can be employed in the process provided by this invention is likewise very broad and can be represented without limitation by the following examples which are intended for illustrative purposes only:

5. aromatic acids in which the acid group is attached to an aromatic carbocyclic ring, examples of which include benzoic acid, any phenylbenzoic acid, the naphthoic acids, and other fused aromatic ring systems bearing a carboxyl group; the phenyl or other aromatic ring systems, in addition to the carboxyl group, may bear one or more substituents of the type noted in (1).

6. alkyl acids in which the acid group is attached to an open chain, saturated or unsaturated alkyl group, examples of which include acetic acid, propionic acid, butyric acid, valeric acid, caproic acid, caprylic acid, myristic acid, palmitic acid. The alkyl moiety may contain one or more substituents of the type noted in (1).

7. aralkyl acids such as phenylacetic acid and phenylpropionic acid. The aromatic ring to which the carboxyl group is attached may be a single ring (e.g., phenyl) or fused ring system, and the ring(s) may be substituted with one or more substituents of the type noted in (1).

8. aromatic heterocyclic acids, in which the heterocyclic ring can optionally be attached to or fused with a non-heterocyclic ring such as any of the pyridine carboxylic acids, benzimidazole carboxylic acids, benzthiazole carboxylic acids, quinozaline carboxylic acids, pyrimidine carboxylic acids, and so forth.

9. non-aromatic heterocyclic acids such as any of the piperidine carboxylic acids, piperazine carboxylic acids, morpholine carboxylic acids, pyrrolidine carboxylic acids, and quinuclidine carboxylic acids.

The invention is also applicable to reactants having mixed functionality, such as to amino acids as previously noted. "Amino acids" as a group is intended to include not only the twenty or so commonly known α-amino acids, but also other amino acids as well, such as the various piperidine carboxylic acids.

Given the simplicity of making amides by the process of this invention, an additional utility is to employ the coupling reagent and process herein provided to synthesize various test compounds which are amides in various biological screens predictive of pharmaceutical indications. Because of the ease with which the coupling agent can be employed and with which workup can be effected, the reagents and methods herein are well suited to making mixtures of compounds for high throughput screening.

The invention is illustrated by the following examples which are solely for the purpose of illustration and are not to be taken as limiting. In the examples, it is noted that yields are typically over 80% of theoretical, although lower yields were encountered on occasion.

EXAMPLE 1

This example illustrates an optimized procedure for making a solid phase coupling reagent according to the invention.

Twenty grams (g) of 1-ethyl-3-(3-dimethylamino-propyl)carbodiimide (EDC, obtained as the hydrochloride salt from Sigma Chemical) was converted to the free base as follows. The EDC was added to a separatory funnel containing 200 mL of methylene chloride and about 150 mL of water. The water and organic layers were shaken together while adding 10% aqueous ammonium hydroxide solution in increments ultimately sufficient to maintain the aqueous layer basic to pH paper. The methylene chloride layer was separated and the aqueous layer was re-extracted with about 100 mL of additional methylene chloride. The methylene chloride layers were combined, washed twice with 150 mL portions of water, and dried by filtering through a bed of anhydrous magnesium sulfate. The dried methylene chloride solution of EDC was then evaporated to dryness on a rotary evaporator to yield 15.66 g (100.9 mmole) of the free base as an oil. $^1$H NMR showed no evidence of any impurities.

The free base EDC produced as above was dissolved in approximately 500 mL of DMF. To this EDC solution was added 105.1 g of 200–400 mesh chloromethylated polystyrene resin (obtained from Peptides International) calculated to contain a total loading of 84.06 eq. of chloromethyl groups. About 300 mL of additional DMF was added and the reaction mixture was heated at 100° C. overnite with stirring. The mixture was then cooled, vacuum filtered, and the solid phase coupling reagent product washed 3 times with additional (150–200mL portions of) DMF. The coupling reagent was then washed three times with THF (150–200 mL portions) and three times with diethyl ether (150–200 mL portions). The final coupling reagent product was then dried in a dessicator over phosphorous pentoxide.

EXAMPLE 2

In a 2-dram vial was placed 650 mg of solid phase coupling reagent, made as in Example 1, together with 4 mL of chloroform. 0.24 mmole of β-alanine in 240 μl of chloroform, blocked at its N-terminus with t-BOC (abbreviated simply as "BOC" in the formulae which follow), was added to the vial. Benzylamine (0.20 mmole, neat) was then added and the vial was stoppered and shaken overnite at room temperature on a plate shaker. The reaction mixture was then gravity filtered through glass wool. 3 mL of chloroform was added to the residual resin, the mixture was shaken on a plate shaker for 10 minutes, and the additional chloroform was filtered through the glass wool. This wash procedure was repeated three times. The chloroform/product mixture was then evaporated to dryness to yield 45.4 mg (81.5% yield) of the product. The product is indicated in Table 1 below as Example 2.

EXAMPLES 2–13

Various carboxylic acid-functional reactants and amino-functional reactants were coupled to make amide products, by the procedure described above for Example 2, except that blocking groups were required only for Examples 2 and 3, with the conventional blocking group t-butoxycarbonyl (BOC) being employed.

It is noted that in examples 6–10 and 13, the hydrogen attached to the indole nitrogen is much less reactive than the other amine hydrogens available, and thus effectively did not participate in the formation of an amide bond, consistent with the $^1$H NMR data obtained.

Table I summarizes the reactants and products. $^1$H NMR data is given in Table 3, infra.

TABLE 1

| EXAMPLE NO. | CARBOXYLIC ACID | AMINE | PRODUCT |
|---|---|---|---|
| 2 | BOC-HN-CH₂CH₂-COOH | H₂N-CH₂-C₆H₅ (benzylamine) | 3-N-BOC-amino-N-benzylpropionamide |
| 3 | BOC-HN-CH₂CH₂-COOH | H₂N-CH₂CH₂-(pyrrolidin-1-yl) | 3-N-BOC-amino-N-(2-pyrrolidin-1-ylethyl)-propionamide |
| 4 | benzoic acid (PhCOOH) | 2-(3,4-dimethoxyphenyl)ethylamine | N-[2-(3,4-dimethoxyphenyl)ethyl]benzamide |
| 5 | 3,3-diphenylpropionic acid | 5-amino-3-methylisoxazole | N-(3-methylisoxazol-5-yl)-3,3-diphenyl-propionamide |

TABLE 1-continued

| EXAMPLE NO. | CARBOXYLIC ACID | AMINE | PRODUCT |
|---|---|---|---|
| 6 | benzo[b]thiophen-3-yl-acetic acid | 5-methoxytryptamine | 2-benzo[b]thiophen-3-yl-N-[2-(5-methoxy-1H-indol-3-yl)ethyl]acetamide |
| 7 | benzo[b]thiophen-3-yl-acetic acid | 2-(3,4-dimethoxyphenyl)tryptamine | 2-benzo[b]thiophen-3-yl-N-{2-[2-(3,4-dimethoxyphenyl)-1H-indol-3-yl]ethyl}-acetamide |
| 8 | 3-(2-chlorophenyl)-5-methylisoxazole-4-carboxylic acid | 5-methoxytryptamine | 3-(2-chlorophenyl)-5-methylisoxazol-4-carboxylic acid [2-(5-methoxy-1H-indol-3-yl)ethyl]amide |

TABLE 1-continued

| EXAMPLE NO. | CARBOXYLIC ACID | AMINE | PRODUCT |
|---|---|---|---|
| 9 | (3-(2-chlorophenyl)-5-methylisoxazole-4-carboxylic acid) | (2-(3,4-dimethoxyphenyl)-1H-indol-3-yl)ethylamine | 3-(2-chlorophenyl)-5-methylisoxazole-4-carboxylic acid {2-[2-(3,4-dimethoxyphenyl)-1H-indol-3-yl]ethyl}amide |
| 10 | (1-benzyl-5-oxo-4-phenylpyrrolidin-2-yl)acetic acid | 2-(5-methoxy-1H-indol-3-yl)ethylamine | 2-(1-benzyl-5-oxo-4-phenylpyrrolidin-2-yl)-N-[2-(5-methoxy-1H-indol-3-yl)ethyl]-acetamide |

TABLE 1-continued

| EXAMPLE NO. | CARBOXYLIC ACID | AMINE | PRODUCT |
| --- | --- | --- | --- |
| 11 | benzoic acid (PhCOOH) | 2,2-diphenylethylamine | N-(2,2-diphenylethyl)benzamide |
| 12 | 3,3-diphenylpropanoic acid | tetrahydrofurfurylamine | 3,3-diphenyl-N-(tetrahydrofuran-2-yl-methyl)propionamide |
| 13 | 1-benzyl-5-oxo-4-phenylpyrrolidine-2-acetic acid | 2-[2-(3,4-dimethoxyphenyl)-1H-indol-3-yl]ethylamine | 2-(1-benzyl-5-oxo-4-phenylpyrrolidin-2-yl)-N-{2-[2-(3,4-dimethoxyphenyl)-1H-indol-3-yl]ethyl}-acetamide |

EXAMPLES 14–19

The following examples illustrate the applicability of the invention to amide formation as set forth in Table 2 from amines having secondary amine nitrogens.

Each of the following amines and carboxylic acids were reacted in the manner described in Example 2, except that no protective groups were required, to produce the named product.

TABLE 2

| EXAMPLE NO. | AMINE | CARBOXYLIC ACID | PRODUCT |
|---|---|---|---|
| 14 | 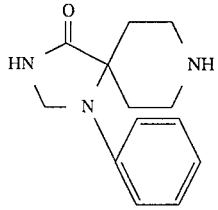 | 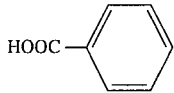 | 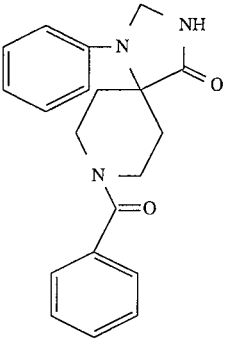<br>8-benzoyl-1-phenyl-1,3,8-tri-azaspiro[4.5]-decan-4-one |
| 15 | 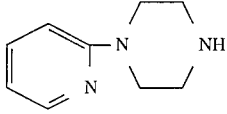 | 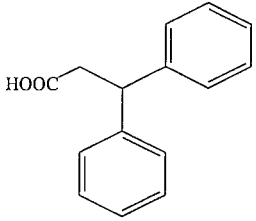 | 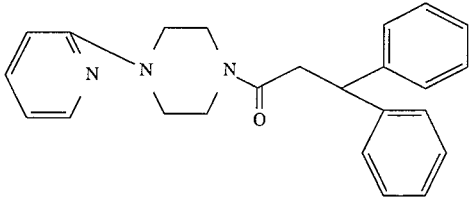<br>3,3-diphenyl-1-(4-pyridin-2-ylpiperazin-1-yl)propan-1-one |
| 16 | 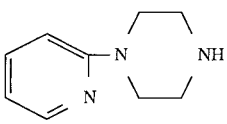 | 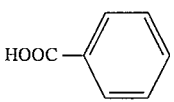 | 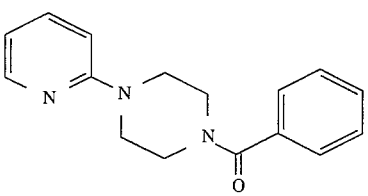<br>phenyl-(4-pyridin-2-yl-piperazin-1-yl)-methanone |
| 17 | 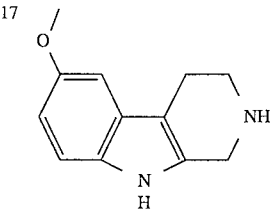 | 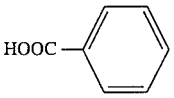 | 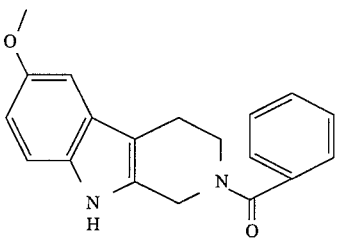<br>6-methoxy-1,3,4,9-tetrahydrocarbolin-2-yl)-phenyl-methanone |

TABLE 2-continued

| EXAMPLE NO. | AMINE | CARBOXYLIC ACID | PRODUCT |
|---|---|---|---|
| 18 | (structure) | (structure) | (structure) 1-[1-(2-benzo[b]-thiophen-3-ylacetyl)-piperidin-4-yl-1,3-dihydrobenzimidazol-2-one |
| 19 | (structure) | (structure) | (structure) 1-benzyl-5-[2-(3,4-dihydro-1H-isoquinolin-2-yl)-2-oxoethyl]-3-phenylpyrrolidin-2-one |

$^1$H NMR data for Examples 2–20 shown in Table 3 below.

TABLE 3

| EXAMPLE NO. | $^1$H NMR |
|---|---|
| 2 | 1.4(s, 9H); 2.40(t, J=6Hz, 2H); 3.38(q, J=6Hz, 2H); 3.40(d, J=6Hz, 2H); 5.23(bs, 1H); 6.35 (bs, 1H); 7.15–7.4(m, 5H) |
| 3 | 1.36(bs, 9H); 1.70–1.74(m, 4H); 2.32(t, J=6Hz, 2H); 2.47 (bs, 4H); 2.53(t, J=6Hz, 2H); 3.27–3.37(m, 4H); 5.48(bs, 1H); 6.34(bs, 1H) |
| 4 | 2.83(t, J=7Hz, 2H); 3.63(q, J=7Hz, 2H); 3.78(s, 3H); 3.81 (s, 3H); 6.4(bs, 1H); 6.70–6.79 (m, 3H); 7.32–7.43(m, 3H); 7.65–7.68(m, 2H) |
| 5 | 2.15(s, 3H); 3.06(d, J=8Hz, 1H); 4.44(t, J=8Hz, 1H); 4.44 (bs, 1H); 4.94(s, 1H); 7.1–7.35 (m, 10H) |
| 6 | 2.76(t, J=7Hz, 2H); 3.47(q, J=7Hz, 2H); 3.83(s, 3H); 3.95 (s, 2H); 5.44(bs, 1H); 6.38(bd, J=2Hz, 1H); 6.8–7.5(m, 7H); 7.80(d, J=8Hz, 1H); 7.93(s, 1H) |
| 7 | 3.00(t, J=7Hz, 2H); 3.48(q, J=7Hz, 2H); 3.73(s, 2H); 3.85 (s, 3H); 3.86(s, 3H); 3.93(s, 1H); 5.59(t, J=7Hz, 1H); 6.75–7.8(m, 11H); 8.59(s, 1H) |
| 8 | 2.72(s, 3H); 2.76(t, J=7Hz, 2H); 3.60(q, J=7Hz, 2H); 3.82 (s, 3H); 3.84(s, 3H); 5.32(t, J=7Hz, 1H); 6.64(d, J=2Hz, 1H); 6.83–6.87(m, 2H); 7.1–7.3 (m, 5H); 8.23(s, 1H) |
| 9 | 2.66(s, 3H); 2.96(t, J=7Hz, 2H); 3.33(q, J=7Hz, 2H); 3.85 (s, 3H); 3.89(s, 3H); 5.28(t, 3H, J=6Hz); 6.9–7.5(m, 11H); 8.48(s, 1H) |
| 10 | 2.04(dd, J=8, 14Hz, 1H); 2.12–2.2(m, 2H); 2.40(dd, J=5, 14Hz, 1H); 2.84(t, J=8Hz, 2H); 3.4–3.6(m, 2H); 3.65(t, J=9Hz 1H); 3.79(s, 3H); 4.0(m, 1H); 3.97(d, J=15Hz, 1H); 4.85(d, J=15Hz, 1H); 6.10(t, J=6Hz, 1H); 6.81(dd, J=2, 9Hz, 1H); 6.85(d, J=2Hz, 1H); 6.98(d, J=2Hz, 1H); 7.05–7.4(m, 10H); 8.55(s, 1H) |
| 11 | 4.08–4.14(m, 2H); 4.37(t, J=8Hz, 1H); 6.23(bs, 1H); 7.2–7.6(m, 15H) |
| 12 | 1.15–1.26(m, 1H); 1.63–1.80(m, 3H); 2.89(dd, J=3, 8Hz, 2H); 3.05–3.18(m, 1H); 3.32–3.40(m, 1H); 3.50–3.80(m, 3H); 4.58(t, J=8Hz, 1H); 5.74(bs, 1H); 7.1–7.4(m, 10H) |
| 13 | 1.91(dd, J=9.0, 15Hz, 1H); 2.05–2.2(m, 2H); 2.32(dd, J=5.0, 15 Hz, 1H); 3.06 (t, J=7Hz, 2H); 3.4–3.55(m, 2H); 3.62(t, J=9Hz, 1H); 3.81(s, |

TABLE 3-continued

| EXAMPLE NO. | $^1$H NMR |
|---|---|
|  | 3H); 3.86(s, 3H); 3.83–4.0(m, 2H); 4.8(d, J=15Hz, 1H); 5.73 (t, J=6Hz, 1H); 6.83(d, J=8Hz, 1H); 7.0–7.4(m, 15H); 7.55(d, J=8Hz, 1H); 8.63(s, 1H) |
| 14 | 1.64–1.68(bd, 1H); 1.85–1.89 (bd, 1H);2.48(bt, 1H); 2.68(bt, 1H); 3.55–3.78(m, 2H); 3.88(bt, 1H); 4.72(bs, 3H); 6.79(d, J=8Hz, 2H); 6.90(t, J=7Hz, 1H); 7.2–7.5(m, 7H); 8.13(s, 1H) |
| 15 | 3.10(d, J=8Hz, 2H); 3.28–3.47 (m, 6H); 3.63–3.70(m, 2H); 4.71 (t, J=8Hz, 1H); 6.56(d, J=8Hz, 1H); 6.60–6.67(m, 1H); 7.10–7.30(m, 10H); 7.43–7.51(m, 1H); 8.15–8.21 (m, 1H) |
| 16 | 3.54(bs, 6H); 3.87(bs, 2H); 6.64(m, 2H); 7.4(s, 5H); 7.48 (J=2, 7Hz, 1H); 8.17(m, 1H) |
| 17 | 2.79(bt, 2H); 3.71(bt, 2H); 3.84 (s, 3H); 4.91(bs, 2H); 6.79(dd, J=2, 9Hz, 1H); 6.92(bs, 1H); 7.14(bd, J=9Hz, 1H); 7.47(bs, 5H); 8.66(bs, 1H) |
| 18 | 1.5–1.7(m, 2H); 1.78(bd, J=13Hz, 1H); 2.11(ddd, J=4, 12, 15Hz, H); 2.69(t, J=13Hz, 1H); 3.12(bt, J=9Hz, 1H); 4.05 (d, J=14Hz, 1H); 4.15(s, 2H); 4.4–4.6(m, 1H); 4.91(bd, J=14Hz, 1H); 6.51(complex d, 1H); 6.9–7.4(m, 8H); 10.5(bs, 1H) |
| 19 | 2.25–2.5(m, 3H); 2.65–2.9(m, 3H); 3.3–3.6(m, 1H); 3.7–3.9(m, 1H); 4.1–4.4(m, 3H); 4.66(s, 1H); 4.87(dd, J=8, 15Hz, 1H); 7.1–7.5(m, 14Hz) |

What is claimed is:

1. A method of preparing an amide, comprising reacting an amino group-bearing compound with a carboxyl group-bearing compound in the presence of a solid phase coupling reagent comprising an insoluble polymer bearing pendant side chains, said side chains each comprising a terminal portion having the formula $$-N^+(CH_3)_2(CH_2)_n-N=C=N-CH_2-CH_3 \quad Y^- \qquad (I)$$

wherein $Y^-$ is a counteranion and n is an integer of 2–6.

2. A method as defined in claim 1, wherein n is 3.

3. A method as defined in claim 1, wherein said insoluble polymer is polystyrene crosslinked with divinyl benzene.

4. A method of synthesizing a peptide comprising reacting a first compound having the formula $P^1$—NH—$R^1$—COOH with a second compound having the formula $H_2N$—$R^2$—COO—$P^2$ in the presence of an insoluble polymer bearing pendant side chains, wherein each side chain comprises a terminal portion having the formula:

$$-\underset{\underset{CH_3}{|}}{\overset{\overset{CH_3}{|}}{N^+}}-(CH_2)_n-N=C=N-CH_2-CH_3 \quad Y^-$$

wherein $P^1$ and P2 represent an amino protecting group and a carboxyl protecting group, respectively;

$R^1$, together with the amino and carboxyl group to which it is bonded, represents an amino acid or a peptide;

$R^2$, together with the amino and carboxyl group to which it is bonded, represents an amino acid or a peptide;

Y is a counteranion; and n is an integer of 2–6.

5. A method as defined in claim 4, wherein n is 3.

6. A method as defined in claim 4, wherein said polymer is polystyrene crosslinked with divinyl benzene.

* * * * *